United States Patent
Noda et al.

[11] Patent Number: 5,737,383
[45] Date of Patent: Apr. 7, 1998

[54] METHOD AND APPARATUS FOR AUTOMATICALLY TESTING TIRE

[75] Inventors: Yuichi Noda; Kenji Nakamura, both of Hiratsuka, Japan

[73] Assignee: The Yokohama Rubber Co. Ltd., Tokyo, Japan

[21] Appl. No.: 626,991

[22] Filed: Apr. 3, 1996

[30] Foreign Application Priority Data

Apr. 24, 1995 [JP] Japan .................................. 7-098921

[51] Int. Cl.⁶ .......................................... G01B 15/06
[52] U.S. Cl. ...................................... 378/61; 378/57
[58] Field of Search ........................... 378/62, 61, 57

[56] References Cited

U.S. PATENT DOCUMENTS 3,883,744  5/1975  Steffel ........................... 73/146
5,060,250  10/1991  Kwee et al. ...................... 378/61
5,083,306  1/1992  Steffel ........................... 378/61

*Primary Examiner*—Don Wong
*Attorney, Agent, or Firm*—Nikaido, Marmelstein, Murray & Oram LLP

[57] ABSTRACT

A tire includes at least a pair of breaker plies each having a plurality of wire codes of different orientation. In a tire testing apparatus, a tire is loaded to a test position and electromagnetic wave having a wavelength equal to or shorter than X-ray is irradiated to transmit a tread surface of one of test portions of the tire loaded at the test position. A detector detects the electromagnetic wave to produce a test image signal. A measuring section executes a processing of at least one test item on the pair of breaker plies to a test image data and automatically determines whether the test position of the tire is defective or non-defective, from the processing result of the test image data. A control section determines whether all the test portions of the tire are tested, when the tire is determined to be non-defective at the one test portion, issues a rotate command to rotate the tire for another test position if all the test portions of said tire are not yet ended, and issues a first unload command if all the test portions are ended.

20 Claims, 19 Drawing Sheets

METHOD AND APPARATUS FOR AUTOMATICALLY TESTING TIRE

BACKGROUND OF THE INVENTION

1. Field of the Invention

The present invention relates to a method and apparatus for testing a tire, and more particularly, to a method and apparatus for automatically testing the internal structure of a tire using an electromagnetic wave such as X-ray having a short wavelength.

2. Description of Related Art

FIG. 13 is a diagram showing the typical internal structure of a tire 200. Referring to FIG. 13, the tire 200 is composed of a thick tread section 212 contacting the ground, a shoulder section 216, a thin side wall section 214 and a rim cushion section 206 in an external view. The internal structure of the tire 200 is mainly composed of a carcass ply 208, breaker plies 210 (210a, 210b), and beads 202. The tread section 212 is a thick rubber layer covering a carcass ply 208 and breaker plies 210 and has resistance against abrasion, cut and shock to protect the carcass ply 208 and breaker plies 210. The carcass ply 208 is an important portion functioning as a framework of the tire and endures the weight, shock and air pressure which acts on the tire. The beads 202 prevent deformation of the tire 200 due to the air pressure and external force and functions to fix the tire to the rim to prevent the vibration of the tire 200 during rotation. The breaker plies 210 are interposed between the carcass ply 208 and the tread 202 and has the effect of "hoop" on the carcass ply 208. As shown in FIG. 14, two breaker plies 210 are rubber stripe plies and used together as a pair. A large number of wire cords 211 (211a and 211b) are buried in parallel to each other in the breaker plies 210 (210a and 210b), respectively. The orientation of the wire cord 211a is different from that of the wire cord 211b. As shown in FIG. 15, the breaker plies 210a and 210b have different widths and the breaker ply 211b is narrower than the breaker ply 211a. The breaker ply 211b is adhered on the central portion of the breaker ply 210a which is adhered on the carcass ply 208. Therefore, in testing the tire 200 structured as described above, the arrangement of breaker plies 210 and the arrangement state of wire cords 211 are specifically important.

Conventionally, the tire 200 is tested by picking up X-ray having transmitted the tire 200 and by observing the picked up image of the tire 200 by a person in charge of test. In this manner, conventionally, there is a problem in that since the tire 200 is tested by the person with a long time, the test results is possibly different a person by a person.

SUMMARY OF THE INVENTION

The present invention is made in the light of the above-mentioned problem and has, as an object, to provide a method and apparatus for automatically testing a tire with a short time and a high precision.

In order to achieve an aspect of the present invention, a tire includes at least a pair of breaker plies disposed between a carcass and a tread, each of the breaker plies includes a plurality of wire cords provided with a substantially constant gap between the wire cords, and an orientation of each wire cord in one of the breaker plies is different from that of each wire cord in the other. The tire test apparatus of the present invention includes a driving section for loading and holding a tire to a testing position in response to a test command, for rotating the tire at the test position in response to a rotate command, and for unloading the tire to a first position in response to a first unload command, an emitting section for emitting electromagnetic wave having a wavelength equal to or shorter than X-ray, a detecting section for detecting the electromagnetic wave having transmitted one of test portions of the tire which is loaded at the test position, and for outputting the detecting result as a test image signal, a measuring section for receiving the test image signal from the detecting section, for executing a processing of at least one test item on the pair of breaker plies to produce a test image data corresponding to the test image signal, and for determining whether the pair of breaker plies is defective or non-defective, based on the processing result and a reference data for the at least one test item, and a control section for outputting the test command to the driving section, for determining whether all the test portions of the tire are tested, when the tire is determined to be non-defective at the one test portion, for outputting the rotate command to the driving section for a next test portion if all the test portions of the tire are not yet tested, and for outputting the first unload command to the driving section if all the test portions are tested.

In this case, the control section may output a second unload command to the driving section when the tire is determined to be defective at the one test portion. The driving section unloads the tire at a second position in response to the second unload command. The measuring section includes a plurality of measuring units for respectively measuring the tire on a plurality of test items, and the plurality of measuring units are operable independently from each other. The at least one test item is at least one of: whether breaker plies are arranged to have a linearity at an edge section of the breaker ply, whether any of the wire cords of the breaker ply protrudes from the edge section of the breaker ply, whether a gap greater than a predetermined value is present between breaker plies having the same wire cord orientation, whether the breaker plies having the same wire cord orientation overlap at a connection section of them, whether any of wire cords is broken or untied in the edge section of the breaker ply, whether the breaker plies of the pair are arranged inversely with respect to left and right positions, whether an alien substance is introduced in the breaker ply or between the breaker plies of the pair, whether displacement of one breaker ply from another breaker ply is present, and whether the wire cords or rubber sections overlap in the breaker ply.

In order to achieve another aspect of the present invention, a method of testing a tire, comprising the steps of:

loading a tire to a test position, a tire including at least a pair of breaker plies disposed between a carcass and a tread, each of the breaker plies including a plurality of wire cords provided with a substantially constant gap between the wire cords, and an orientation of each wire cord in one of the breaker plies being different from that of each wire cord in the other;

irradiating electromagnetic wave having a wavelength equal to or shorter than X-ray to transmit a tread surface of one of test portions of the tire loaded at the test position;

detecting the electromagnetic wave to produce a test image signal;

executing a processing of at least one test item on the pair of breaker plies to a test image data; and automatically determining whether the tire is defective or non-defective, from the processing result of the test image data.

In order to achieve still another aspect of the present invention, an apparatus for an internal structure of a tire, the tire including at least a pair of breaker plies disposed between a carcass and a tread, each of the breaker plies including a plurality of wire cords provided with a substantially constant gap between the wire cords, and an orientation of each wire cord in one of the breaker plies being different from that of each wire cord in the other, includes an output unit for outputting a test result, an emitting section for emitting electromagnetic wave having a wavelength equal to or shorter than X-ray, a detecting section for detecting the electromagnetic wave having transmitted one of test portions of the tire which is loaded at the test position, and for outputting the detecting result as a test image signal, a measuring section for receiving the test image signal from the detecting section, for executing a processing of at least one test item on the pair of breaker plies to produce a test image data corresponding to the test image signal, and for determining whether the pair of breaker plies is defective or non-defective, based on the processing result and a reference data for the at least one test item, and a control section for controlling the emitting section, the detecting section and the measuring section for testing all the test positions, and for outputting to the output unit a data indicating that the tire is non-defective when the tire is determined to be non-defective at all the test positions.

In the measuring section, the test image data is converted into a binary image data and whether the edge portion of the breaker ply is distorted is determined based on a line set on the binary image data. A reference image data may be generated from the test image data and the reference image data is subtracted from the test image data, and whether the breaker ply is defective or non-defective is determined based on the subtracted image data. Densities of pixels corresponding to the wire cords may be inverted and whether the breaker with the same orientation of the wire cords plies overlap is determined based on an image data having the inverted densities. Densities of pixels corresponding to the wire cords may be inverted for every predetermined distance and whether the breaker plies with the same orientation of the wire cords overlap or whether the breaker plies provided to separate from each other is determined based on an image data having the inverted densities. Pixels corresponding to the wire cords may be deleted and whether an alien substance is introduced based on an image data having the inverted densities. Pixels corresponding to the wire cords may be deleted and whether the wire cords or rubber sections overlap may be determined based on an image data having the remaining pixels. Further, the test image data may be converted into a binary image data and whether the edge portion of the breaker ply is distorted in part, whether the two breaker plies are displaced and arranged, or whether the two breaker plies overlap is determined based on a line set on the binary image data and change of the densities.

DESCRIPTION OF THE PREFERRED EMBODIMENTS

The tire testing apparatus of the present invention will be described below with reference to the accompanying drawings.

Figure 1:
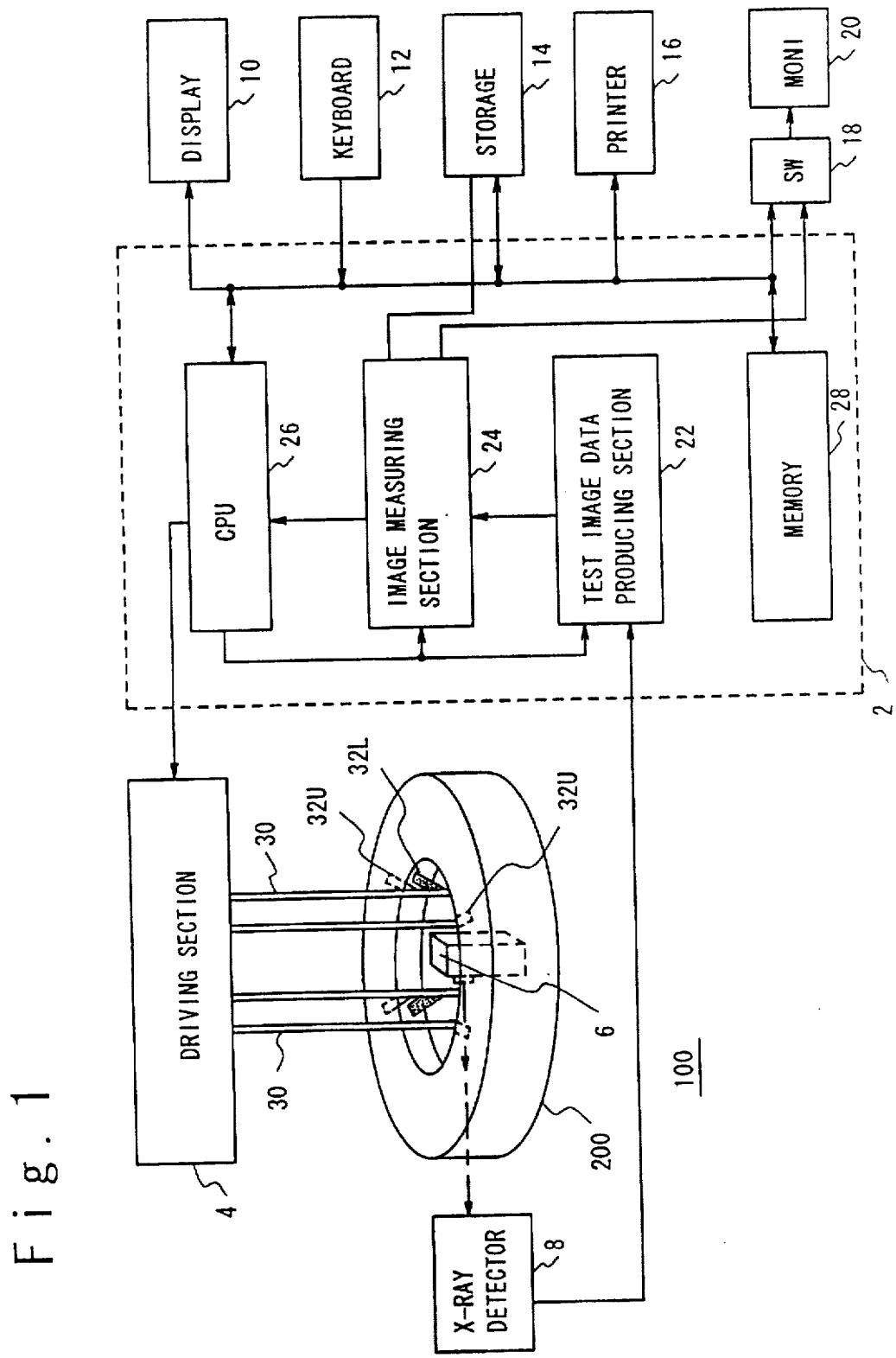
FIG. 1 is a block diagram of a tire testing apparatus according to an embodiment of the present invention.

FIG. 1 is a block diagram illustrating the tire testing apparatus 100 according to an embodiment of the present invention. Referring to FIG. 1, a circuit portion 2 of the tire testing apparatus 100 includes a CPU 26 for controlling the operation of the whole apparatus. A driving section 4 carries and holds a tire 200 to be tested from a first position (not shown) to a predetermined test position shown in the figure in response to a command from the CPU 26. The driving section 4 has four arms 30 to each of which holding sections 32U and 32L are attached. The driving section 4 decreases the distances between the arms 30 to insert the arms 30 in the tire 200. Then, the distances between the arms 30 are extended until each of the arms 30 collides with the beads 202 of the tire 200. When the arms contact the bead, the holding section 32U of each arm is moved upward and the holding section 32L is moved downward such that the holding sections 32U and 32L contact the inside of the beads 202. Thus, the driving section 4 can hold the tire 200 and carry it in the held state. The arms 30 are rotatable. The driving section 4 rotates the arms 30 in response to a command from the CPU 26 so that the tire 200 is rotated. An X-ray source 6 irradiates X-ray in response to a command from the CPU 26. The X-ray is irradiated to tire 200, transmits through the tire 200, and is detected by a detector 8. In the embodiment the X-ray is used. However, electromagnetic wave having wavelengths shorter than the X-ray may be used. The detector 8 outputs an image signal to the above-mentioned circuit section 2 in accordance with the detecting result.

The circuit section 2 is composed of a test image data producing section 22, an image measuring section 24, the above-mentioned CPU 26 and a memory 28. The CPU is connected to a display unit 10, a keyboard 12, a storage unit 14, an image printer 16, a switch 18 which are all provided outside of the circuit section, in addition to the driving section 4, the X-ray source 6, the memory 28, the test image data producing section 22 and the image measuring section 24. A monitor 20 is connected to the switch 18. The storage unit 14 and the switch 18 are also connected to the image measuring section 24. The test image data producing section 22 produces a test image data from the image signal supplied from the detector 8, in response to a command from the CPU 26. The image measuring section 24 processes the test image data in response to a command from the CPU 26 and determines whether the tire 200 is defective or non-defective, based on an allowance data read out from the storage unit 14. The image measuring section 24 outputs the determining result to the CPU 26. In the memory 28 are data and a program to be executed by the CPU 26. The CPU 26 executes the program stored in the memory 28 in response to a command inputted from a user via the keyboard 12. When receiving the determining result from the image measuring section 24, the CPU 26 outputs it to the image printer 16 and displays it on the display unit 10. The CPU 26 switches the switch 18 when a switching command is inputted via the keyboard 12, or based on the program to be executed by the CPU 26, if necessary. Thereby, a selected one of the processes in the image measuring section 24 is outputted to the monitor 20.

Figure 2:
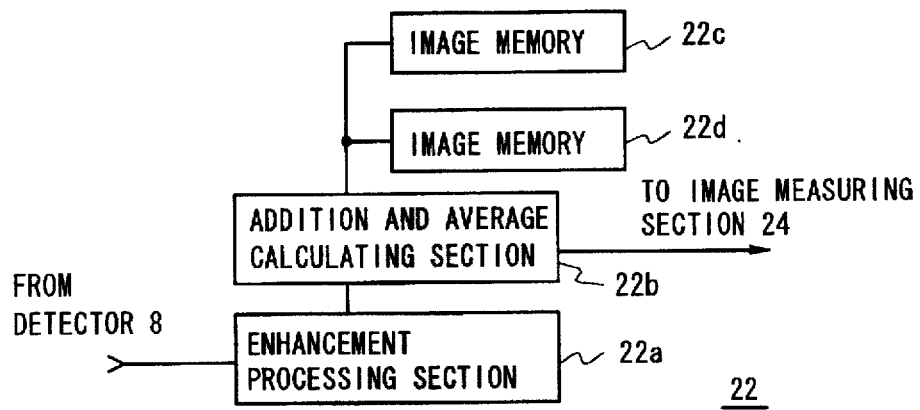
FIG. 2 is a block diagram showing the structure of a test image data producing section shown in FIG. 1.

FIG. 2 is a block diagram illustrating the test image data producing section 22. Referring to FIG. 2, the producing section 22 is composed of an enhancement processing section 22a for amplifying and digitalizing the analog image signal supplied from the detector 8 after removing noise from the image signal, such that a transmission loss can be corrected for, an image memory 22c for storing the digital image data, an image data 22d for storing an addition calculation result when the image data stored in the image memory 22c is added, and an adding and averaging processing section 22b for adding the image data of predetermined frames and producing the test image data in which densities of pixels are averaged, by dividing the added image data by the number of frames.

Figure 3:
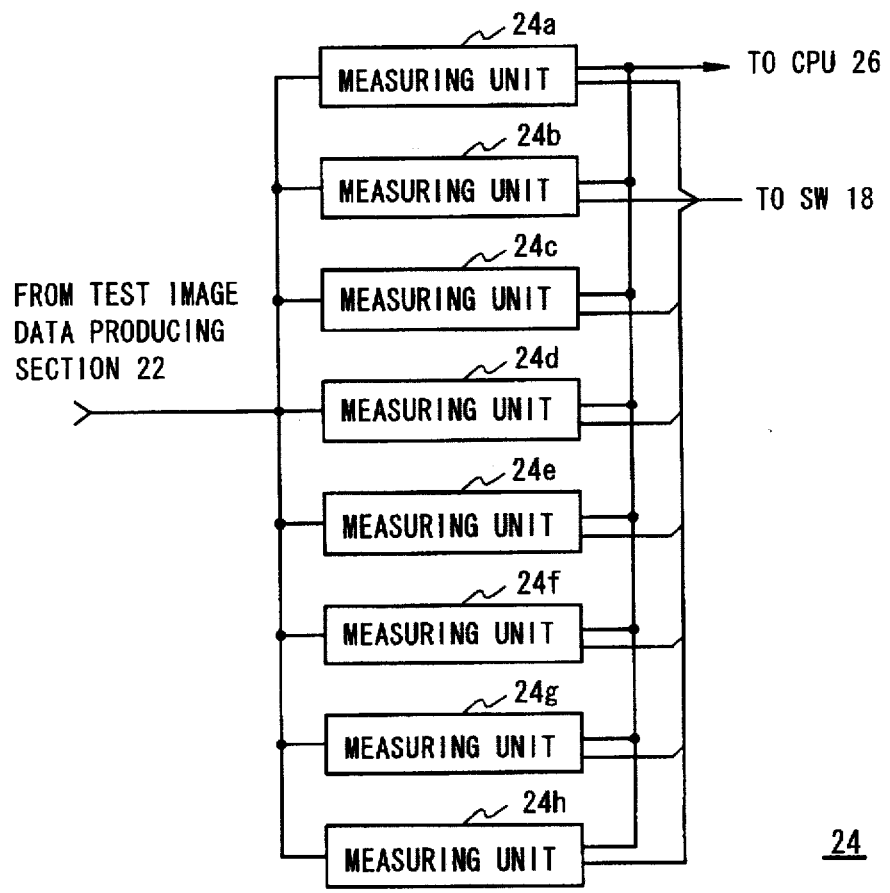
FIG. 3 is a block diagram showing the structure of an image measuring section shown in FIG. 1.
Figure 16:
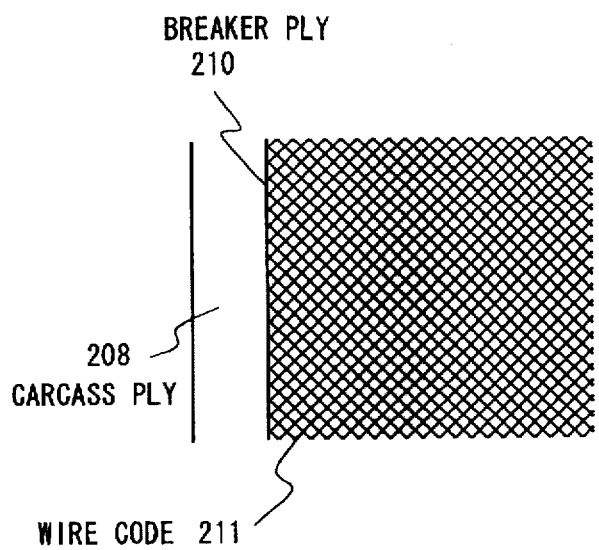
FIG. 16 is a diagram showing the arrangement state in which one breaker ply is adhered to the other breaker ply to align the edge portion of one breaker ply with that of the other breaker ply.
Figure 17:
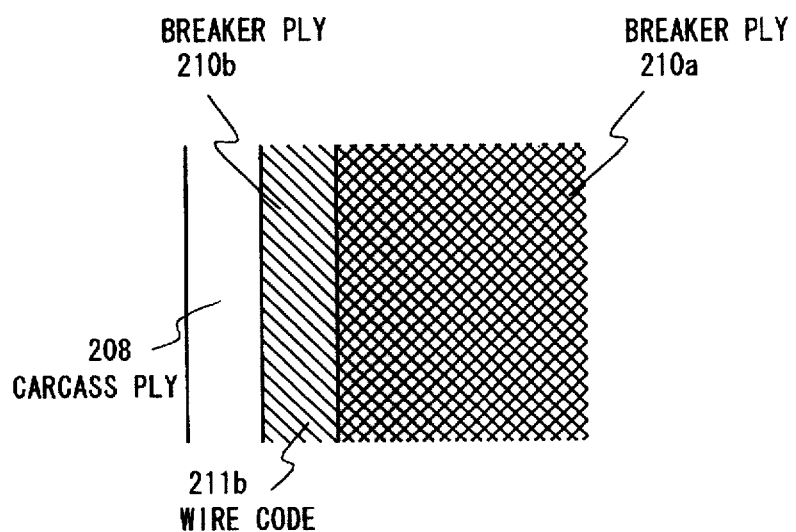
FIG. 17 is a diagram showing the arrangement state in which two breaker plies are adhered to the carcass ply inversely to each other in a lateral direction.
Figure 18:
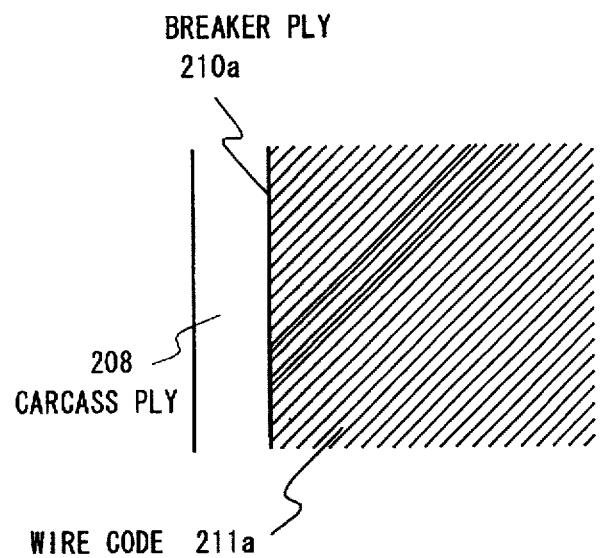
FIG. 18 is a diagram showing the arrangement state in which two breaker plies having wire cords of a same orientation are adhered to the carcass ply to overlap each other in a vertical direction.
Figure 19:
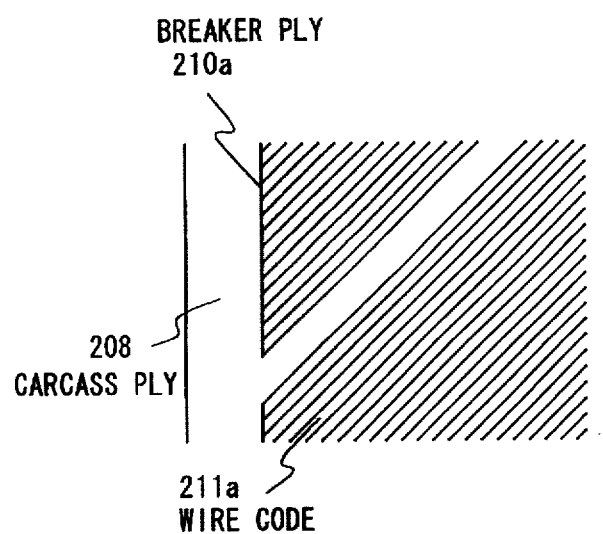
FIG. 19 is a diagram showing the arrangement state in which two breaker plies having wire cords of a same orientation are adhered to the carcass ply to have a space between the two breaker plies in the vertical direction.
Figure 20:
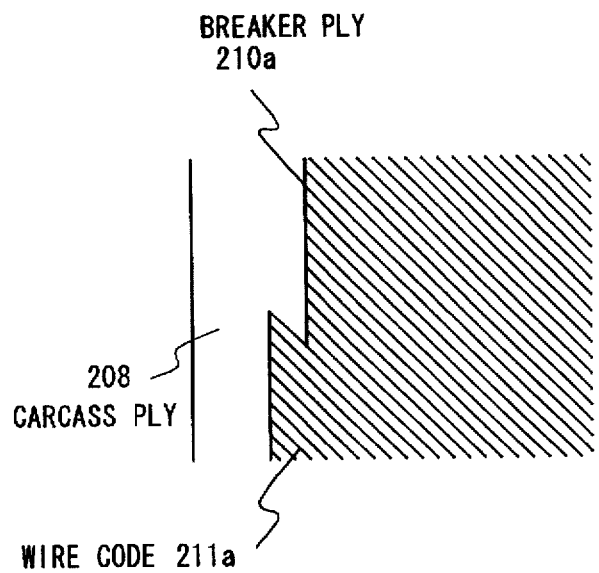
FIG. 20 is a diagram showing the arrangement state in which the positions of wire cords are shifted in a lateral direction between two breaker plies having the wire cords of the same orientation or in a single breaker ply.
Figure 21:
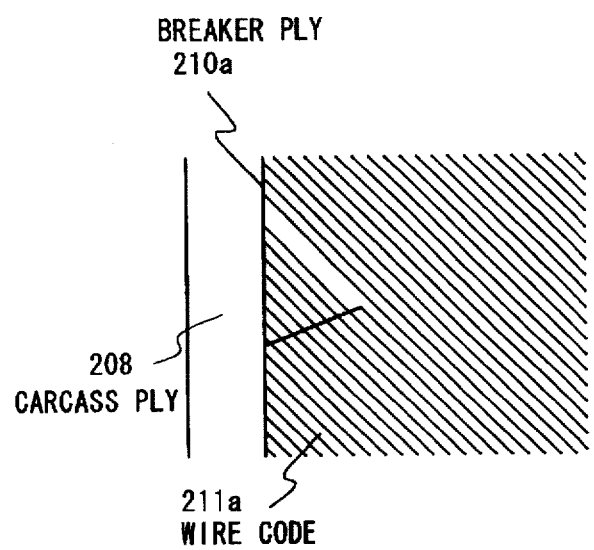
FIG. 21 is a diagram showing the arrangement state in which a wire cord is broken in one breaker ply.
Figure 22:
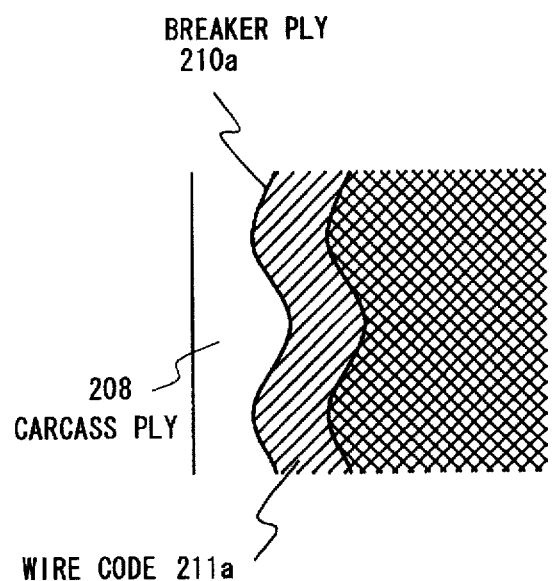
FIG. 22 is a diagram showing the arrangement state in which the vertical edge portion of a breaker ply is in a wave form manner.
Figure 23:
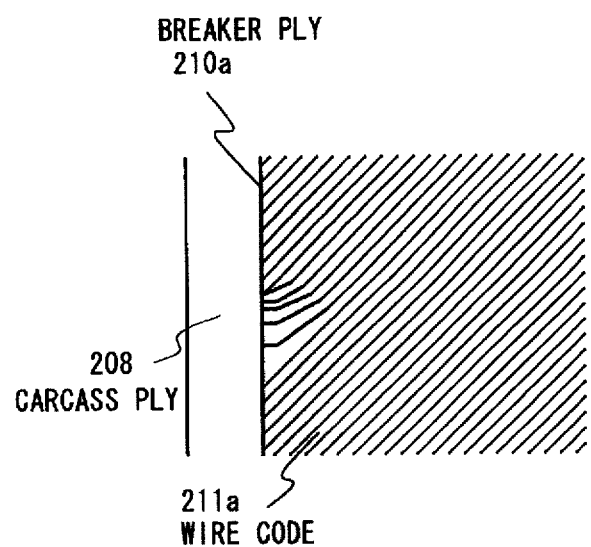
FIG. 23 is a diagram showing the arrangement state in which wire cords are untied in the vertical edge of the breaker ply.
Figure 24:
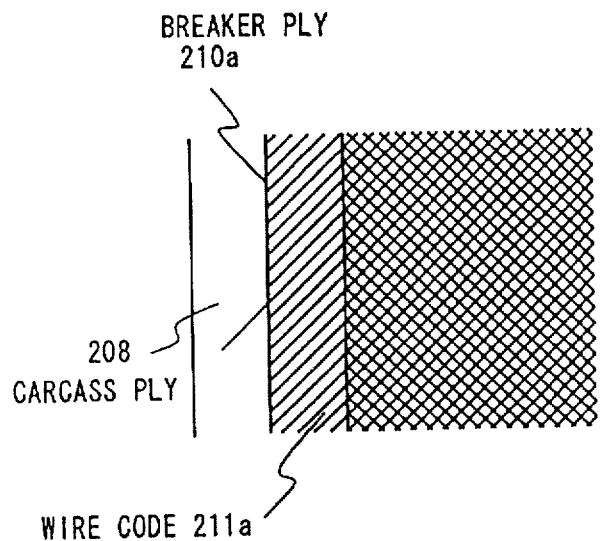
FIG. 24 is a diagram showing the arrangement state in which a wire cord protrudes from the vertical edge portion of one breaker ply.
Figure 25:
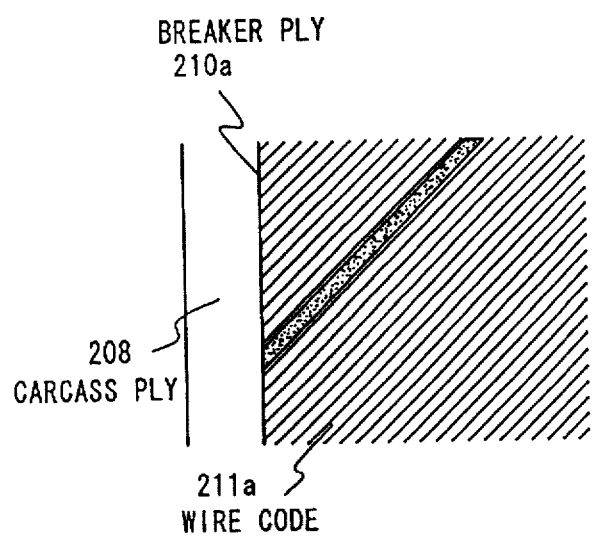
FIG. 25 is a diagram showing the arrangement state in which wire cords or rubber portions overlap in one breaker ply.
Figure 26:
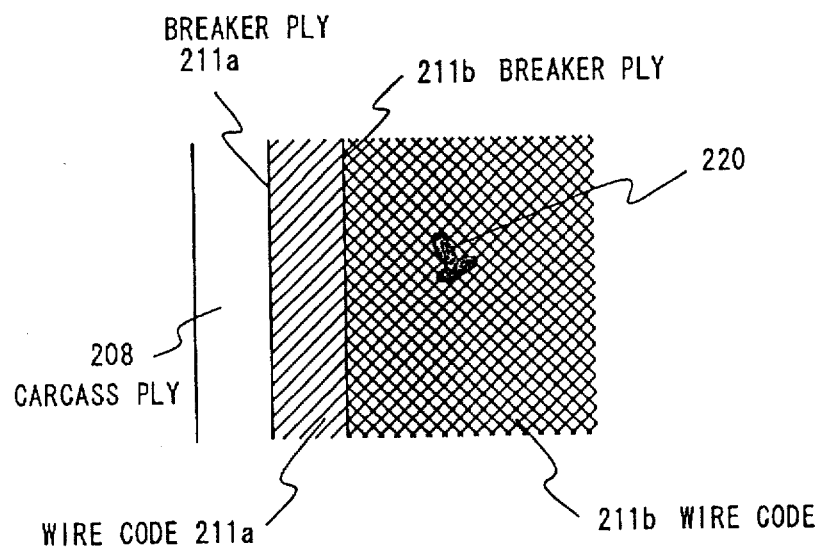
FIG. 26 is a diagram showing the arrangement state in which an alien substance is introduced in one of the breaker plies or between the breaker plies.

FIG. 3 is a block diagram illustrating the detail of image measuring section 24. Referring to FIG. 3, the image measuring section 24 is composed of a plurality of measuring units 24a to 24h. Each of the measuring units 24a to 24h inputs the test image data from the producing section 22 in response to a commend from the CPU 26 to processes it. Also, each measuring unit reads out a reference data or allowance data from the storage unit 14 and determines based on the read out data whether the tire 200 is defective or non-defective. The measuring unit outputs the determining result to the CPU 26. Further, the measuring unit outputs the image during the test processing to the CPU 26 and the switch 18. In the embodiment, the measuring units 24a to 24h test the tire on different test items independently and automatically. Therefore, the test time can be shortened. More particularly, the measuring unit 24a determines whether linearity of the edge portion of a breaker ply 210 is distorted as shown in FIG. 22. The measuring unit 24b determines whether a wire cord 211 protrudes from the vertical edge portion of the breaker ply 210 as shown in FIG. 24. The measuring unit 24b determines whether a wire cord 211 protrudes from the vertical edge of the breaker ply 210 as shown in FIG. 24. The measuring unit 24c determines whether an excess space is present in a connection portion between two breaker plies 210 with the same orientation of wire cords 211 as shown in FIG. 19. The measuring unit 24d determines whether an overlapping portion is present in the connection portion between the two breaker plies 210 with the same orientation of wire cords 211 as shown in FIG. 18. The measuring unit 24e determines whether a wire cord 211 is broken at the edge portion of the breaker ply 210, whether the wire cords 211 are untied at the edge portion of the breaker ply, and whether two breaker plies are arranged inversely to each other in a lateral direction, as shown in FIGS. 21, 23, and 17. The measuring unit 24f determines whether an alien substance is introduced in a breaker ply 210 or between breaker plies 210 as shown in FIG. 26. The measuring unit 24g determines whether wire cords 211 or rubber sections overlap in a breaker ply 210, i.e., whether the breaker ply is defective or non-defective, as shown in FIG. 25. The measuring unit 24h determines whether a breaker ply 210 partially displaces in a lateral direction or two breaker plies displace, as shown in FIG. 20 and whether the breaker plies 210 overlap each other at one edge portion, as shown in FIG. 16.

That is, the measuring unit 24a executes a predetermined density conversion process to the test image data and a filtering process to the test image data after the density conversion process. Thus, contrast of the image is enhanced and a noise component is removed. In the filtering process, the test image data is averaged in pixel density in a predetermined area size unit. The measuring unit 24a converts the image data obtained through the filtering process into a binary image data. The unit 24a compares a data obtained from the binary image data with a reference data read out from the storage unit 14 to determine whether the edge of a breaker ply 210 is distorted.

The measuring unit 24b executes a predetermined density conversion process to the test image data supplied from the producing section 22 and a filtering process to the test image data after the density conversion process. In the filtering process, the test image data is averaged in pixel density in a predetermined area size unit. Thus, contrast of the image is further enhanced and a noise component is further removed. The measuring unit 24b converts the image data obtained through the filtering process into a binary image data. The unit 24b compare a data obtained from the binary image data with a reference data read out from the storage unit 14 to determine whether a wire cord 211 protrudes from the edge of a breaker ply 210.

The measuring unit 24c executes a predetermined density conversion process to the test image data supplied from the producing section 22 and a filtering process to the test image data after the density conversion process. In the filtering process, the test image data is averaged in pixel density in a predetermined area size unit. Also, at the same time, a differential process is executed to the test image data in a predetermined area size unit. Thus, contrast of the image is further enhanced and a noise component is further removed. Further, a portion where the pixel density greatly changes in a given direction is enhanced. The measuring unit 24c converts the image data obtained through the filtering process into a binary image data. The unit 24c compares a data obtained from the binary image data with a reference data read out from the storage unit 14 to determine whether a space greater than a reference value is present in the connection section between two breaker plies 210.

The measuring unit 24d executes a predetermined density conversion process to the test image data supplied from the producing section 22 and a filtering process to the test image data after the density conversion process. In the filtering process, a differential process is executed to the test image data in a predetermined area size unit, like the measuring unit 24c. Thus, contrast of the image is further enhanced and a noise component is further removed. Further, a portion where the pixel density greatly changes in a given area is enhanced. The measuring unit 24d converts the image data obtained through the filtering process into a binary image data. The unit 24d compares a data obtained from the binary image data with a reference data read out from the storage unit 14 to determine whether two breaker plies 210 overlap in the connection section.

The measuring unit 24e executes a predetermined density conversion process to the test image data supplied from the producing section 22 and a filtering process to the test image data after the density conversion process, as in the measuring unit 24c. The measuring unit 24e converts the image data obtained through the filtering process into a binary image data. The unit 24e compares a data obtained from the binary image data with a reference data read out from the storage unit 14 to determine whether wire cord 211 of a breaker ply 210 are untied, whether a wire code is broken, and whether two breaker plies are inversely arranged in right and left positions.

The measuring unit 24f executes a predetermined density conversion process to the test image data supplied from the producing section 22 and a filtering process to the test image data after the density conversion process. The measuring unit 24f converts the image data obtained through the filtering process into a binary image data. The unit 24f compares a data obtained from the binary image data with a reference data read out from the storage unit 14 to determine whether wire cord 211 of a breaker ply 210 are untied, whether an alien substance is introduced in a breaker ply or between breaker plies.

The measuring unit 24g executes a predetermined density conversion process to the test image data supplied from the producing section 22 and a filtering process to the test image data after the density conversion process. In the filtering process, a differential process is executed to the test image data in a predetermined area size unit. Subsequently, the measuring unit 24g calculates densities between the filtered image data and the image data before the filtering process and then executes the density conversion process to the image data obtained from the calculation again. Thus, contrast of the image is further enhanced and a noise component is further removed. Further, a portion where the pixel density greatly changes is enhanced. The measuring unit 24g converts the image data obtained through the second density conversion process into a binary image data. The unit 24g compares a data obtained from the binary image data with a reference data read out from the storage unit 14 to determine whether wire codes 211 or rubber sections overlap in a breaker.

The measuring unit 24h executes a predetermined density conversion process to the test image data supplied from the producing section 22 and a filtering process to the test image data after the density conversion process. In the filtering process, pixel densities of the image data after the density conversion process are averaged in a predetermined area size unit and a differential process is executed to the test image data in a predetermined area size unit. Thus, contrast of the image is further enhanced and a noise component is further removed. Further, a portion where the pixel density greatly changes in a given direction is enhanced. The measuring unit 24h converts the image data obtained through the filtering process into a binary image data. The unit 24h compares a data obtained from the binary image data with a reference data read out from the storage unit 14 to determine whether displacement of the edge of a breaker ply 210 is present.

Next, the operation of the tire testing apparatus according to the embodiment of the present invention will be described with reference to FIGS. 4 to 27C.

Figure 13:
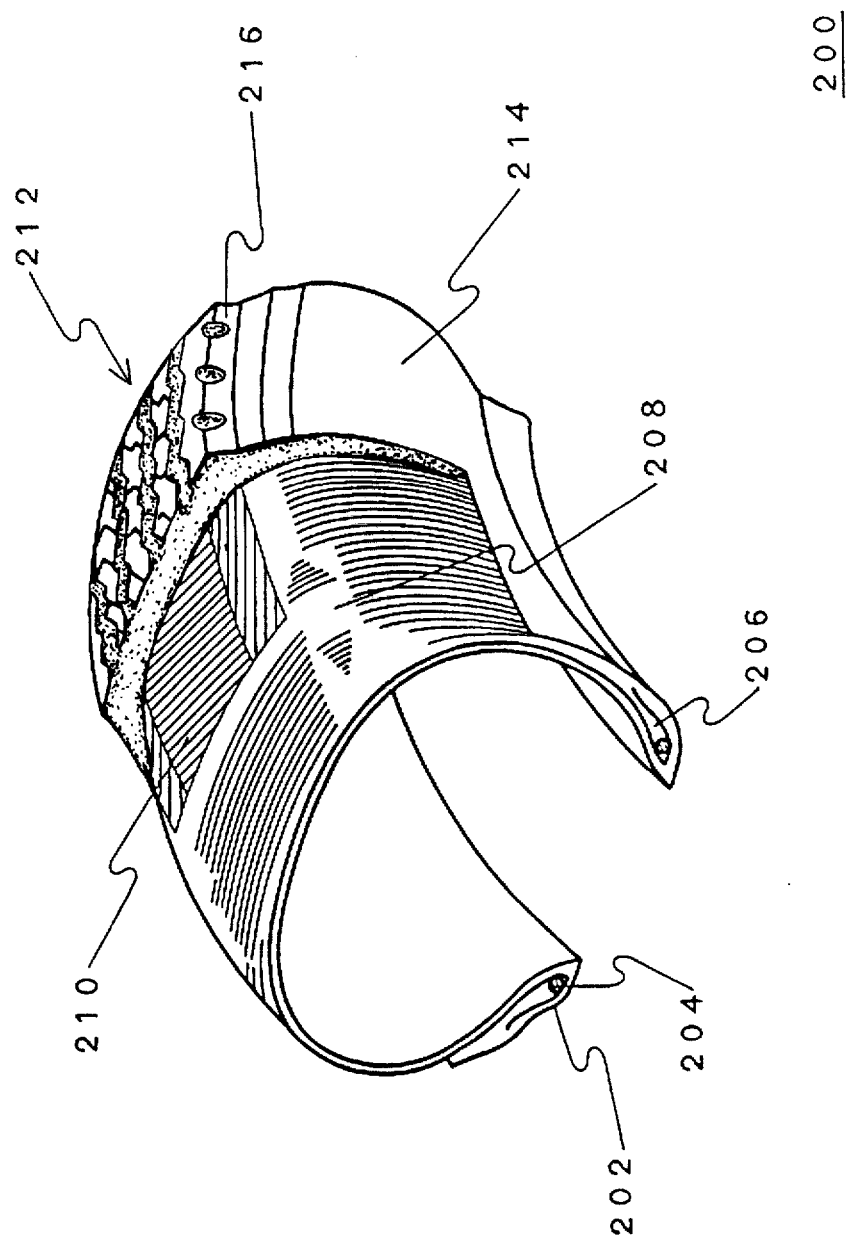
FIG. 13 is a diagram showing the typical internal structure of a tire.
Figure 14:
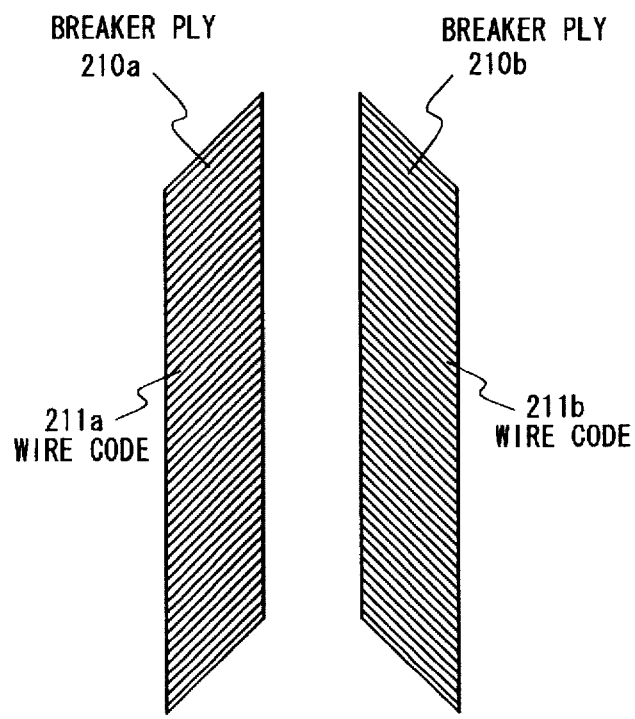
FIG. 14 is a diagram showing a pair of breaker plies.
Figure 15:
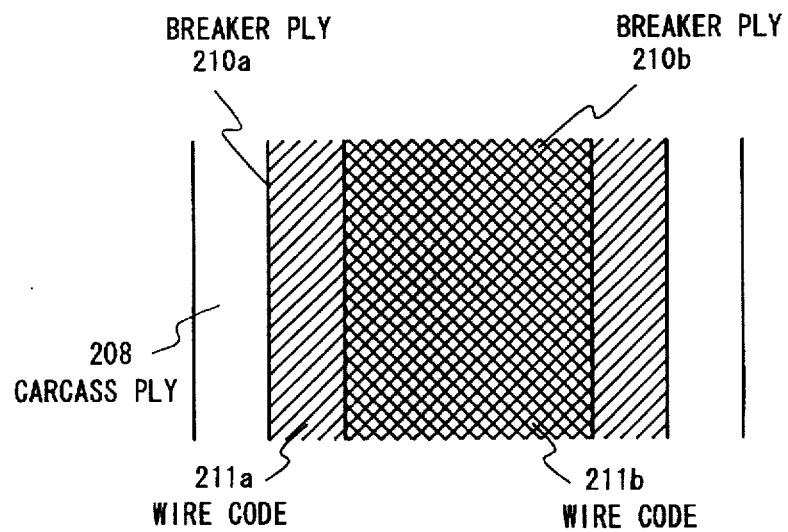
FIG. 15 is a diagram showing the arrangement state in which the pair of breaker plies are adhered to the carcass ply.

The typical internal structure of a tire is shown in FIG. 13. In the embodiment, two breaker plies 210 (210a and 210b) shown in FIG. 14,—the breaker ply 210a is wider than the breaker ply 210b—are attached to a carcass ply 208 such that the breaker ply 210b overlaps the breaker ply 210a at the central portion in a part. Correct arrangement of the breaker plies 210 is shown in FIG. 15. Note that only one breaker ply is shown occasionally for simplification of a figure, although two breaker plies are used in the embodiment. FIG. 16 is a case where two breaker plies 210a and 210b almost completely overlap each other at the edge portions. FIG. 17 is a case where two breaker plies 210a and 210b are arranged inversely in right and left positions. FIG. 18 is a case where two breaker plies 210a and 210a overlap each other in the connection portion of them with a length longer than a specific value. FIG. 19 is a case where a space is present in the connection portion of the two breaker plies 210a and 210a, unlike FIG. 18. FIG. 20 is a case where two breaker plies 210a and 210a are displaced in a lateral direction or one breaker ply 210a is displaced in part. FIG. 21 is a case where a wire cord 211a is broken in a breaker ply 210a. FIG. 22 is a case where breaker plies 210 have a wave form edge portion. FIG. 23 is a case where wire cord 211a are untied in the edge portion of a breaker ply 210. FIG.

24 is a case where a wire cord 211a protrudes from a breaker ply 210a. FIG. 25 is a case where wire cords 211a or rubber sections overlap in a breaker ply 210a. FIG. 26 is a case where an alien substance is present in a breaker ply 210 or between breaker plies 210a and 210b. The tires described above is desirably to be removed. Therefore, the tires are tested by the testing apparatus of the present invention.

First, a tire 200 to be tested is set at a predetermined load position (not shown). When a user operates the keyboard 12 to input a test command, the CPU 26 outputs a load command to the driving section 4. In response to the load command, the driving section 4 inserts four arms 30 into a center portion of the tire 200 in the state in which the distances between the arms 30 are shortened. Then, the arms 30 are moved in a radial direction of the tire 200 by extending the distances between the arms 30. In this case, the holding sections 32U and 32L are in short distance positions. When the arms 30 collide with the beads of the tire 200, the movement of the arms 30 is stopped. Subsequently, the holding sections 32U are moved upward and the holding section 32L are moved downward until these sections collide with the inside walls of the bead section. Thereby, the tire 200 is held by the driving section 4. While holding the tire 200, the four arms 30 are lifted and moved from the load position to a test position and put down, so that the tire 200 is set in the test position. If the load process of the tire 200 is ended, the CPU 26 controls the X-ray source 6 to irradiate X-ray. The X-ray which has transmitted the tire 200 is detected by the detector 8 and the detecting result is supplied to the test image data producing section 22 as an image signal. In the producing section 22, a noise component is removed and the brightness of the image signal is amplified and the amplified image signal is digitalized to produce an image data. A plurality of frames of the image data for the same test portion of the tire 200 are added and the adding result is divided by the number of adding processes to produce a test image data having an averaged density. Thus, the test image data is obtained in which contrast is enhanced and the noise component is removed. The test image data is supplied to the image measuring section 24. In the image measuring section 24, a predetermined density conversion process is executed to the test image data and a filtering process is also executed to the image data after the density conversion process. Thus, the contrast of the image data is further enhanced and a noise component is further removed. In the filtering process, a differential process may be applied. The image data after the filtering process is converted into a binary image data. The binary image data is compared to a predetermined reference data to determine whether the tire 200 is defective or non-defective. The determining result is informed to the CPU 26. If there is no problem on a current testing portion of the tire 200 as a result of the determination in the image measuring section 24, the CPU 26 determines whether all the testing portions of the tire 200 are tested. If all the testing portions are not yet completed, the CPU 26 outputs a rotate command to the driving section 4 for a next testing portion of the tire 200. The driving section 4 rotates the tire 200 in a practical rotation direction of the tire 200 as in response to the rotate command. In this manner, a new testing portion of the tire 200 comes in front of the X-ray source 6. If the test image data indicates any of the examples shown in FIGS. 16 to 26 and as a result of this, the tire 200 is determined to be defective, the CPU 26 outputs a test stop command to the driving section 4. In response to the test stop command, the driving section 4 moves the arms 30 from the testing position to a defective tire position and unloads the tire 200. When the tire 200 is determined to be non-defective on the current testing position by the image measuring section 24 and the CPU 26 determines that all the testing positions of the tire 200 are completely tested, the CPU 26 outputs a test completion command. In response to the test completion command, the driving section 4 moves the arms 30 from the testing position to a non-defective tire position and unloads the tire 200. After a tire 200 to be tested next is located at the load position, the above operation is repeated. This operation is repeated by cycles designated by an input from the keyboard 12.

Next, the detail of test operation of the tire testing apparatus will be described.

Figure 4:
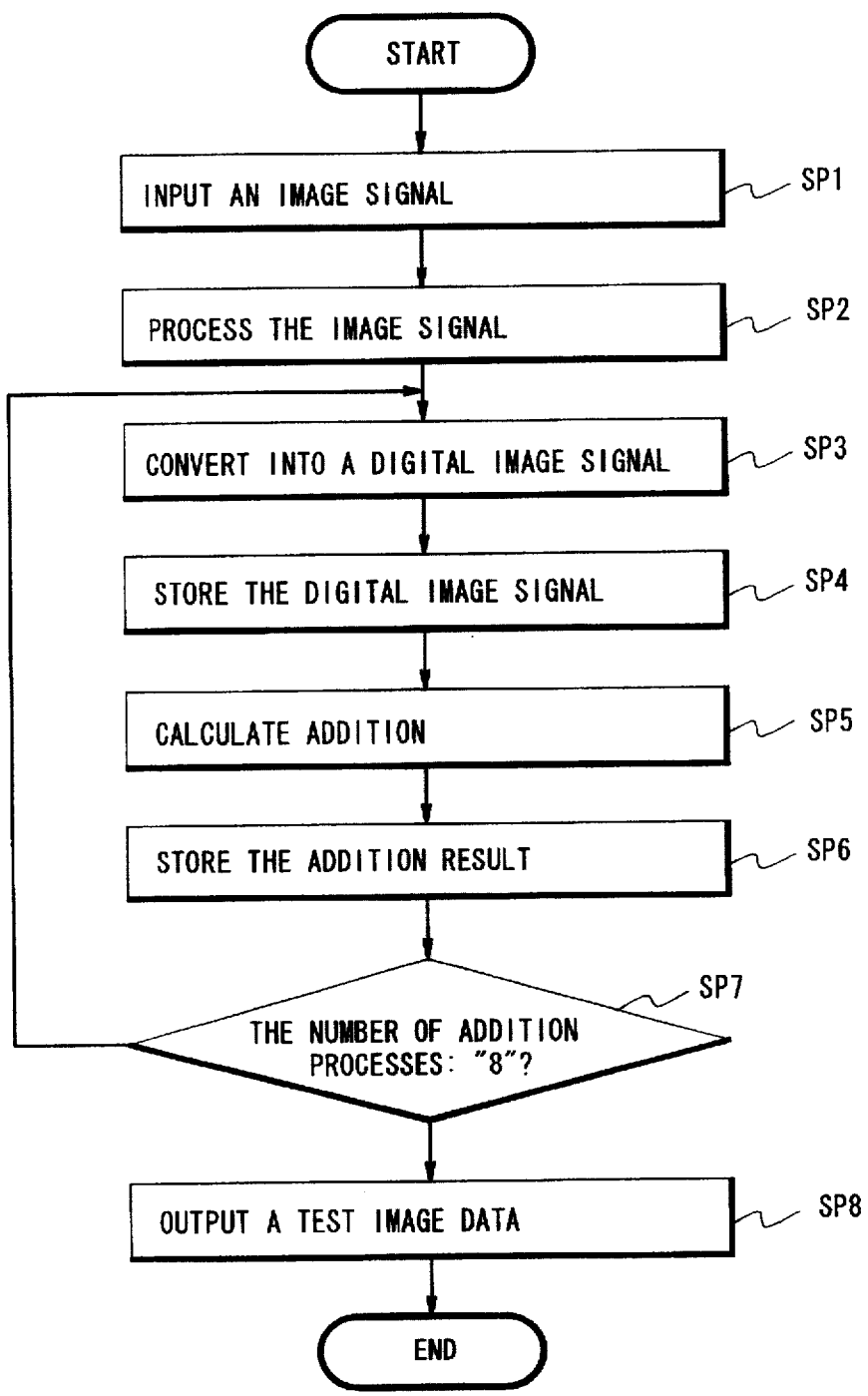
FIG. 4 is a flow chart of the operation of the test image data producing section.

FIG. 4 is a flow chart for explaining the operation of the test image data producing section 22. Referring to FIG. 4, the producing section 22 produces a digital test image data from an analog image signal supplied from the detector 8. At a step SP1, the image signal is inputted from the detector 8 into the processing section 22a. In the processing section 22a, at a step SP2, the image signal is filtered for improvement of image density and removal of noise and then amplified in signal level. The amplified image signal is analog-to-digital converted at a step SP3 to produce a digital image data. Then the digital image data is stored in the image memory 22c in units of frames at a step SP4. Thereafter, when the digital image data for a new frame is stored in the image memory 22c, an image data is read out from in the image memory 22d and added with the image data just stored in the image memory 22c at the step SP5. The adding result is stored in the image memory 22d at a step SP6. At the same time, the number of addition processes is incremented by "1" and whether the number of addition processes is equal to a predetermined value is determined at a step SP7. In the embodiment, the predetermined value is "8". This value is experimentally determined. If the number of addition processes is smaller than "8", the steps SP3 to SP7 are repeated. If the number of addition processes is "8", the image data is read out from the image memory 22d at a step SP8 and divided by "8". As a result, a test image data is obtained and supplied to the image measuring section 24. In order to produce the test image data for one frame, the steps SP3 to SP7 are repeated eight times. The number of times is not limited to "8" and another value is allowed. As a result, image data for frames #1 to #8 are added and image data for #2 to #9 are added. Since the added image data is divided by "8" for averaging, a peak noise component contained in the image data can be decreased.

The image measuring section 24 includes the measuring units 24a to 24h and each of the measuring units 24a to 24h handle the test image data supplied from the test image data producing section 22 in response to a command from the CPU 26.

Figure 5:
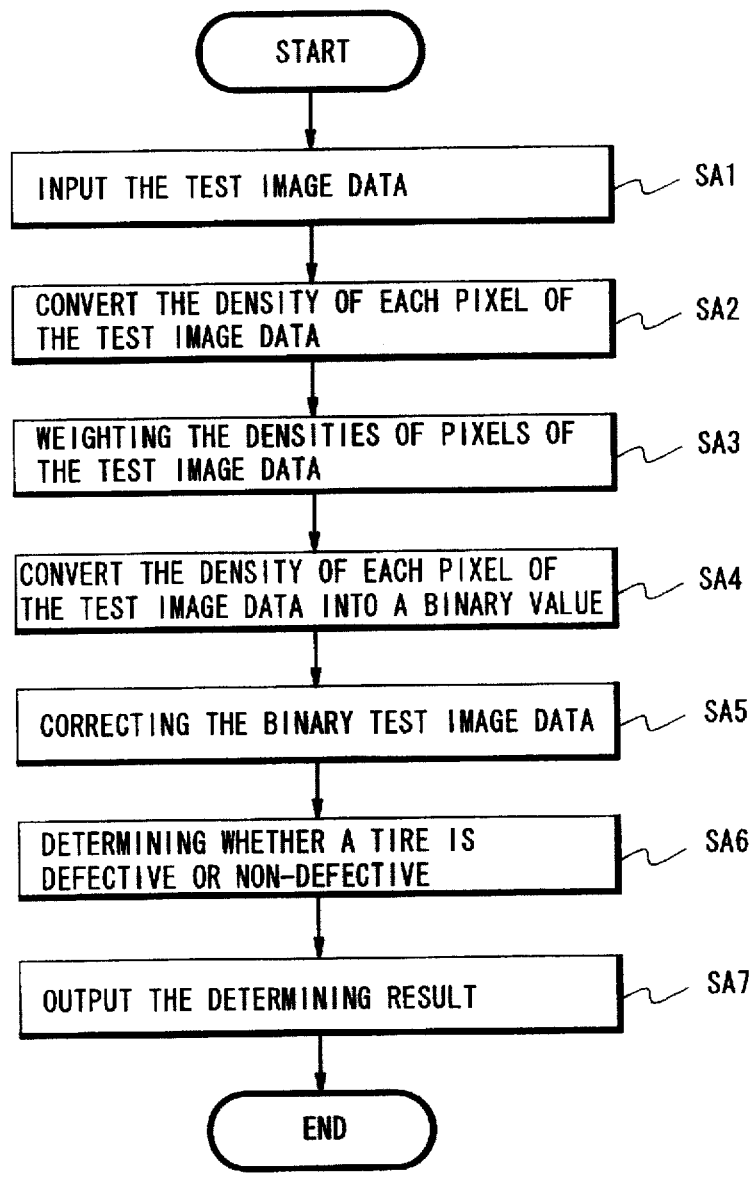
FIG. 5 is a flow chart for explaining the operation of a measuring unit 24a of the image measuring section shown in FIG. 3.
Figures 27A, 27B, 27C:
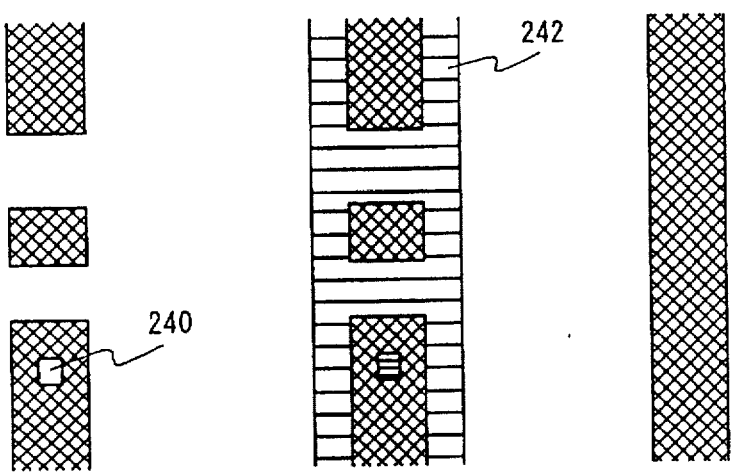
FIG. 27A is a diagram showing a pixel string.
FIG. 27B is a diagram for explaining expansion and filling processing.
FIG. 27C is a diagram for explaining the conversion from a thick pixel string into a thin pixel string.

FIG. 5 is a flow chart illustrating the operation of the measuring unit 24a. Referring to FIG. 5, in the measuring unit 24a, the test image data is inputted from the producing section 22 at a step SA1. The test image data is subjected to a density conversion process at a step SA2. In the density conversion process, the brightness of each pixel of the test image data is inverted, so that wire cords 211 of breaker plies 210 are displayed as black lines. At a step SA3, an averaging process is executed to the brightness inverted image data. In the averaging process, densities of pixels are averaged in units of pixel regions by weighting the densities of pixels of the inverted image data. Thereby, a spike noise component is reduced and the background becomes uniform over the frame of brightness inverted image data. Subsequently, at a step SA4, the averaged image data is converted into a binary image data using a threshold value. The threshold value may be predetermined. Alternatively, the threshold value may be determined based on the pixel density distribution of the averaged image data. Next, at a step SA5, a correcting process is executed to the binary image data. In the correcting process, an expanding process, a filling process and a thin line producing process are included. When the averaged image data is converted into the binary image data, there is a case that an image corresponding to a wire cord 211 of a breaker ply 210 is not a thin line. Also, there is a case that the image has a defect point. For this reason, the image corresponding to the wire cord 211 is expanded. That is, the image is converted into a thick line image. Thus, the image corresponding to the wire cord 211 becomes a continuous line in the most cases. If any defect pixel is remained in the thick line, the pixel is filled, i.e., the pixel is converted into a black dot. Subsequently, the thick line image is converted into a thin line image. More particularly, as shown in FIG. 27B, black pixels are added to a black pixel string shown in FIG. 27A in the expanding process. In the filling process, a white pixel in the expanded pixel string is converted into a black pixel. In the thin line producing process, the thick pixel string is converted into a thin pixel string as shown in FIG. 27C. At a step SA6, whether the edge portion of a breaker ply 210 has a wave form is determined. That is, referring to FIG. 22, a vertical line is assumed on the corrected image data. The number of pixels from an end pixel of each of the wire cords at the edge portion to a corresponding pixel having the same y-coordinate as the end pixel is determined. This processing is repeated over all the pixels on the vertical line. Whether the obtained pixel lengths fall within a region designated based on a reference data as an allowance data which is read out from the storage unit 14 is determined. If the pixel numbers fall within the region, the tire 200 is non-defective. At a step SA7, the determining result is outputted to the CPU 26.

Figure 6:
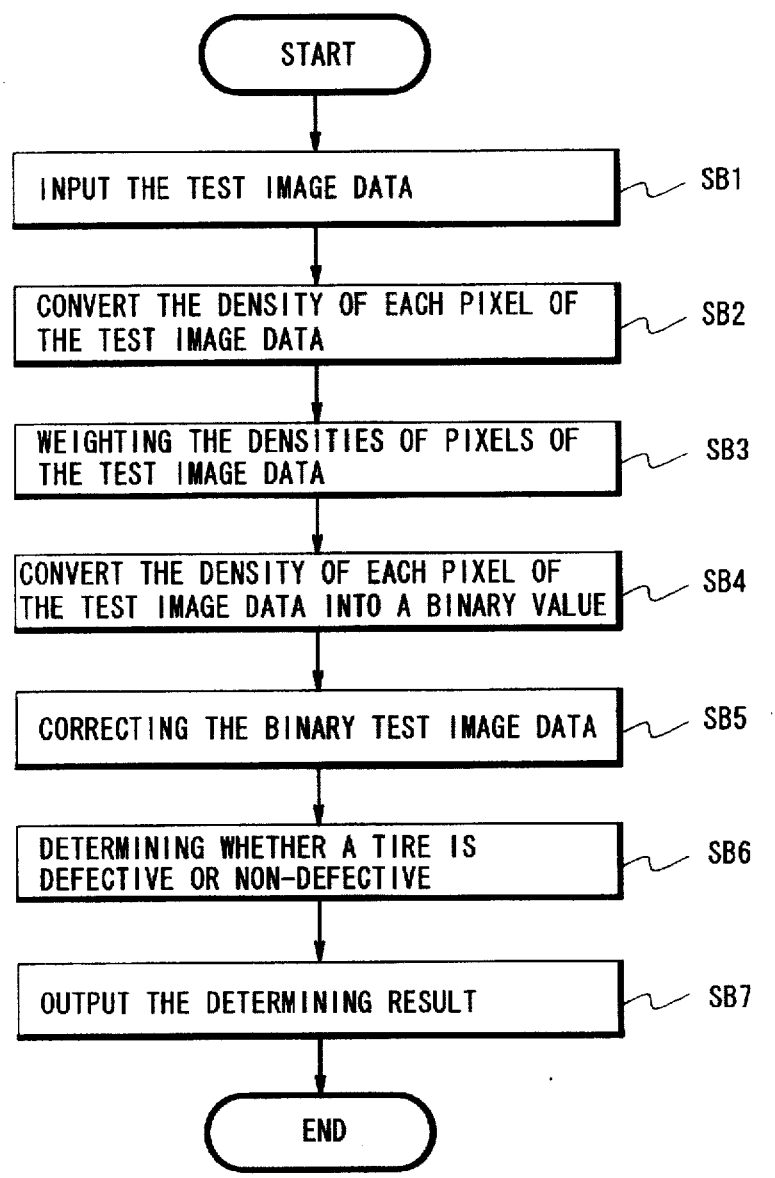
FIG. 6 is a flow chart for explaining the operation of a measuring unit 24b of the image measuring section shown in FIG. 3.

FIG. 6 is a flow chart illustrating the operation of the measuring unit 24b. Referring to FIG. 6, in the measuring unit 24b, the test image data is inputted from the producing section 22 at a step SB1. The test image data is subjected to a density conversion process at a step SB2. In the density conversion process, the brightness of each pixel of the test image data is inverted, so that wire cords 211 of a breaker ply 210 are displayed as black lines. At a step SB3, an averaging process is executed to the brightness inverted image data. In the averaging process, densities of pixels are averaged in units of pixel regions. Thereby, a spike noise component is reduced and the background becomes uniform over the frame of brightness inverted image data. These processes are the same as in the measuring unit 24a. Subsequently, at a step SB4, the averaged image data is converted into a binary image data using a threshold value. Next, at a step SB5, a correcting process is executed to the binary image data. In the correcting process, the expanding process, the filling process and the thin line producing process are included. These steps SB4 and SB5 are the same as the steps SA4 and SA5 in FIG. 5. At a step SB6, whether any wire cord protrudes from the edge portion of a breaker ply 210 is determined. That is, referring to FIG. 24, a vertical line is assumed apart from the edge portion of the breaker ply 210 on the corrected image data. The number of pixels from a pixel on the vertical line to the end point pixel of each of the wire cords is measured over all the pixels on the vertical line. The protrusion is determined if the number of pixels does not fall within a region designated based on a reference data as an allowance data which is read out from the storage unit 14. At a step SB7, the determining result is outputted to the CPU 26.

Figure 7:
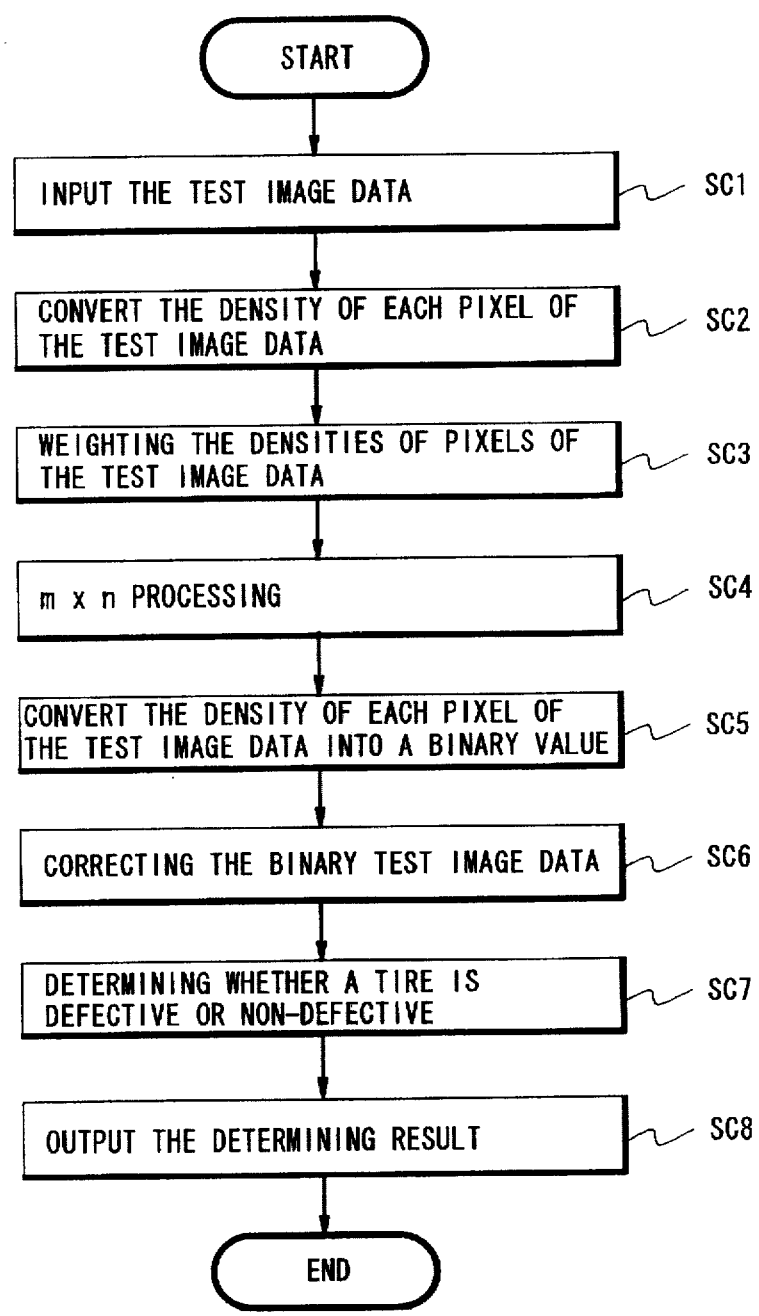
FIG. 7 is a flow chart for explaining the operation of a measuring unit 24c of the image measuring section shown in FIG. 3.

FIG. 7 is a flow chart illustrating the operation of the measuring unit 24c. Referring to FIG. 7, in the measuring unit 24c, the test image data is inputted from the producing section 22 at a step SC1. The test image data is subjected to a density conversion process at a step SC2. In the density conversion process, the brightness of each pixel of the test image data is inverted, so that wire cords 211 of a breaker ply 210 are displayed as black lines. At the same time, a linear conversion process is executed. In the linear conversion, the density X of each pixel is converted into an output Y (=aX+b: a and b are predetermined constants). Conversions such as a quadratic curve conversion ($Y=aX^2+bX+c$), a cubic curve conversion ($Y=aX^3+bX^2+cX+d$), a gamma curve conversion, a log curve conversion ($Y=\log(aX+b)$) and a combination of the conversions may be used (a, b, c and d are predetermined constants). Thereby, the density of each pixel is enhanced. At a step SC3, an averaging process is executed to the brightness inverted image data by weighting the densities of pixels of the inverted image data. The averaging process is the same as the step SA3 in FIG. 5. Next, at a step SC4, an (m×n) process is executed. In the (m×n) process, the densities of pixels in a region of (m×n) pixels are multiplied by predetermined coefficients, so that the image data is differentiated. By selecting the coefficients, lines going from a left upper portion to a right lower portion can be deleted. Similarly, lines going from a left lower portion to a right upper portion can be deleted. After the (m×n) process, at a step SC5, the differentiated image data is converted into a binary image data using a threshold value. Next, at a step SC6, a correcting process is executed to the binary image data. In the correcting process, the expanding process, the filling process and the thin line producing process are included, as in the step SA5 in FIG. 5. That is, the width of a line is changed from 4 pixels to 1 pixel or 5 pixels to 2 pixels, for example. In the correcting process a delete process is further included. In the delete process, a region with a predetermined width around each of lines corresponding to the wire cords 211 is converted into a black pixel region. Therefore, if the wire cords are regularly arranged, the image data would be all black. If the breaker plies are separated too much at the connection portion, a white pixel region would be remained. In this manner, at a step SC7, whether two breaker plies 210 are separated is determined based on whether the number of white pixels is more than a reference data as an allowance data which is read out from the storage unit 14. At a step SC8, the determining result is outputted to the CPU 26.

Figure 8:
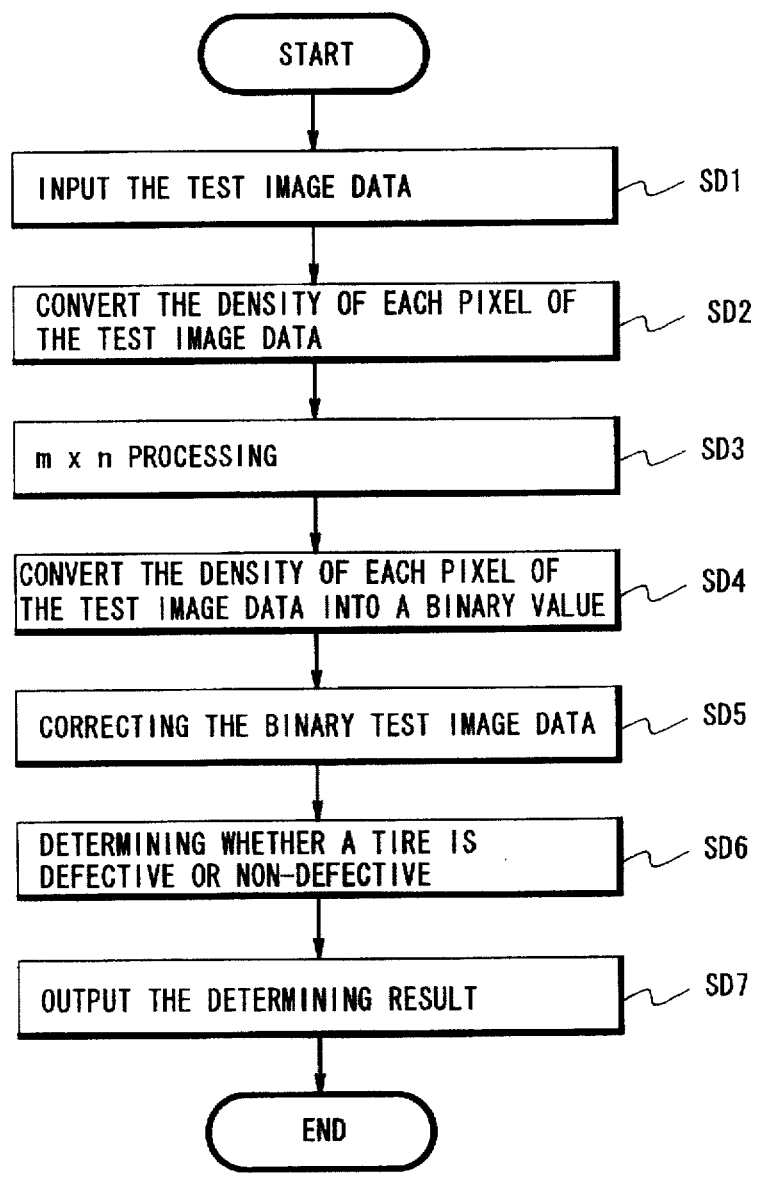
FIG. 8 is a flow chart for explaining the operation of a measuring unit 24d of the image measuring section shown in FIG. 3.

FIG. 8 is a flow chart illustrating the operation of the measuring unit 24d. Referring to FIG. 8, in the measuring unit 24d, the test image data is inputted from the producing section 22 at a step SD1. The test image data is subjected to a density conversion process at a step SD2. In the density conversion process, the brightness of each pixel of the test image data is inverted, so that wire cords 211 of a breaker ply 210 are displayed as black lines. At the same time, a linear conversion process is executed. In the linear conversion, the density X of each pixel is converted into an output Y (=aX+b: a and b are predetermined constants). Conversions such as a quadratic curve conversion ($Y=aX^2+bX+c$), a cubic curve conversion ($Y=aX^3+bX^2+cX+d$), a gamma curve conversion, a log curve conversion ($Y=\log(aX+b)$) and a combination of the conversions may be used (a, b, c and d are predetermined constants). Thereby, the density of each pixel is enhanced. Next, at a step SD3, an (m×n) process is executed. In the (m×n) process, the densities of pixels in a region of (m×n) pixels are multiplied by predetermined coefficients, so that the image data is differentiated. This process is similar to the step SC4. After the (m×n) process, at a step SD4, the differentiated image data is converted into a binary image data using a threshold value. Next, at a step SD5, a correcting process is executed to the binary image data. In the correcting process, the expanding process, the filling process and the thin line producing process are included, as in the step SC6 in FIG. 7. In the correcting process a delete process is further included. In the delete process, a region with a predetermined width around each of lines corresponding to the wire cords 211 is converted into a white pixel region. Therefore, if the wire cords are regularly arranged, the image data would be all white. If the wire cords overlap each other at the connection portion, a black pixel region would be remained. In this manner, at a step SD6, whether two breaker plies 210 overlap is determined based on whether the number of black pixels is more than a reference data as an allowance data which is read out from the storage unit 14. At a step SD7, the determining result is outputted to the CPU 26.

Figure 9:
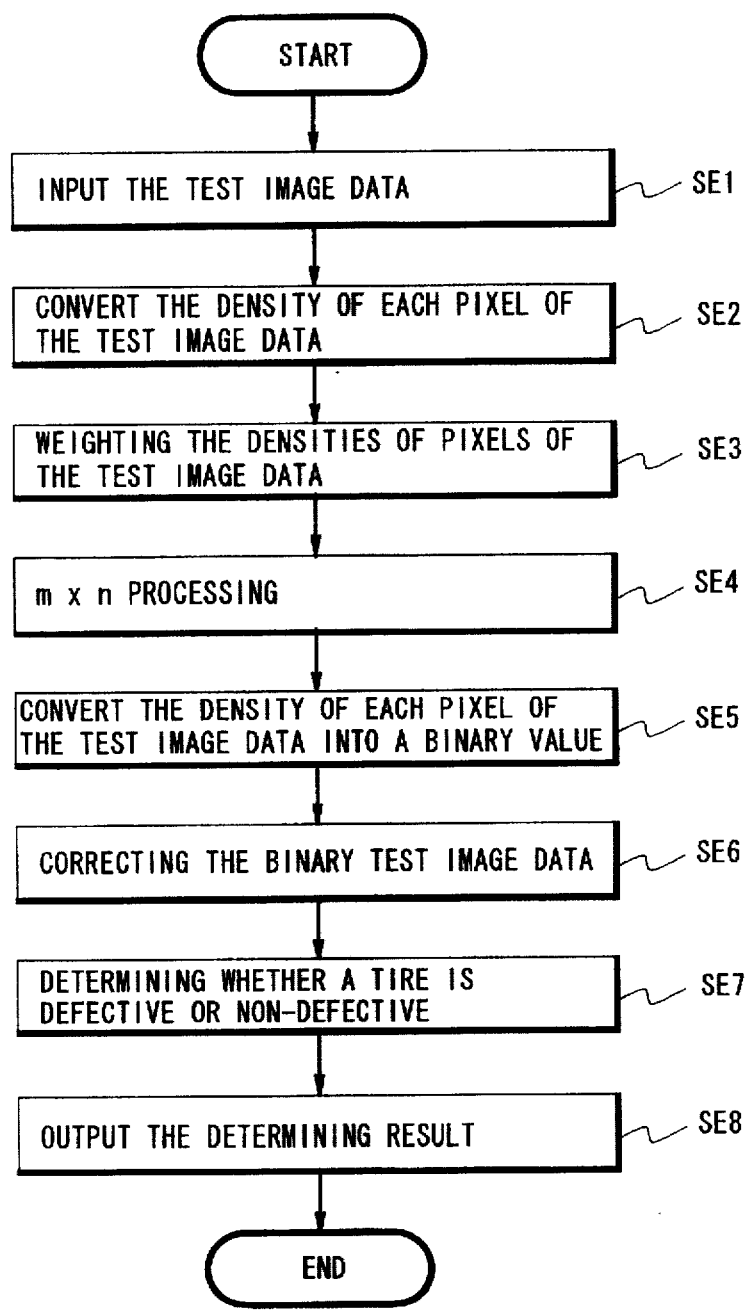
FIG. 9 is a flow chart for explaining the operation of a measuring unit 24e of the image measuring section shown in FIG. 3.

FIG. 9 is a flow chart illustrating the operation of the measuring unit 24e. Referring to FIG. 9, in the measuring unit 24e, the test image data is inputted from the producing section 22 at a step SE1. The test image data is subjected to a density conversion process at a step SE2. In the density conversion process, the brightness of each pixel of the test image data is inverted, so that wire cords 211 of a breaker ply 210 are displayed as black lines. At a step SE3, an averaging process is executed to the brightness inverted image data. These processes are the same as the steps SB1 to SB3 in FIG. 6. Next, at a step SE4, an (m×n) process is executed. In the (m×n) process, the densities of pixels in a region of (m×n) pixels in a region corresponding to a correct breaker ply 211b region are multiplied by predetermined coefficients, so that the image data is differentiated. That is, the image lines with an orientation of the cord wires 211a of the breaker ply 211a are remained and the image lines with another orientation of the wires cords 211b of the breaker ply 210b are deleted. As a result, the image data for one of the two breaker plies 210 can be extracted. After the (m×n) process, at a step SE5, the differentiated image data is converted into a binary image data using a threshold value. Next, at a step SE6, a correcting process is executed to the binary image data. These processes are the same as in the steps SD4 and SD5. In this manner, at a step SE7, whether two breaker plies 210 are arranged inversely in a lateral direction, whether the wire cords are untied, or whether a wire cord is broken is determined based on whether the number of black pixels is more than a reference data as an allowance data which is read out from the storage unit 14. At a step SE8, the determining result is outputted to the CPU 26.

Figure 10:
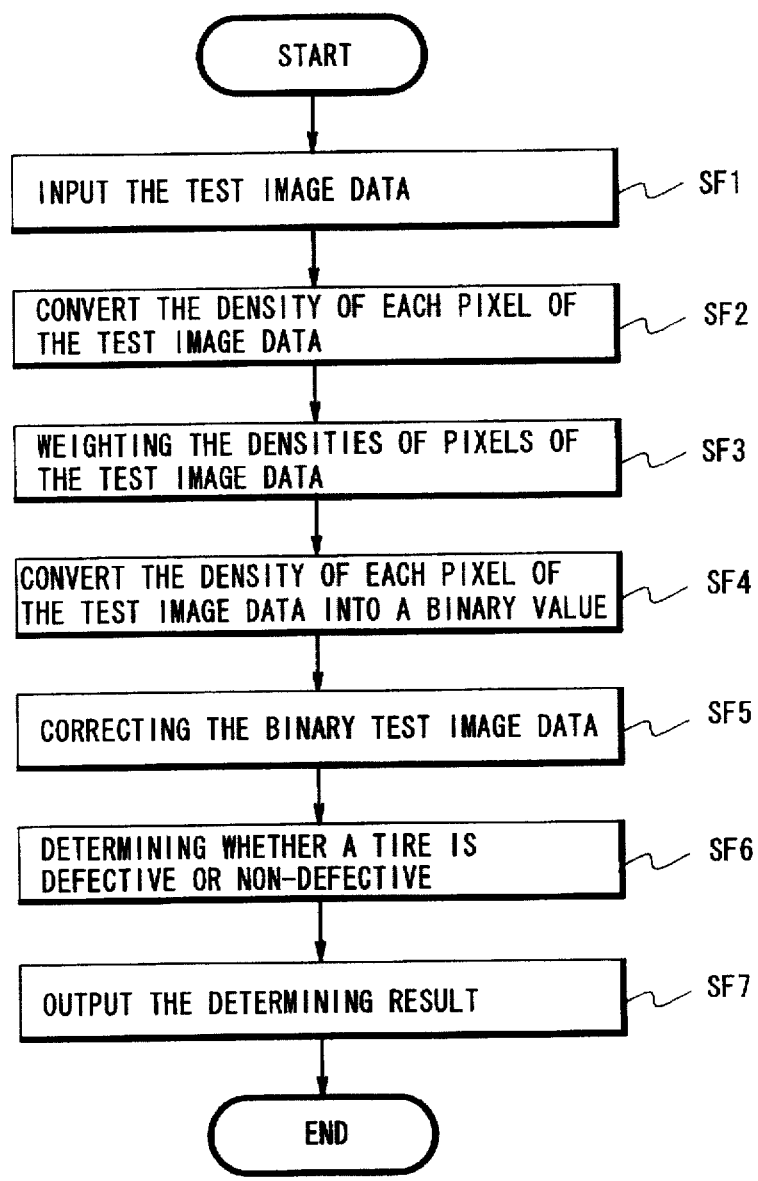
FIG. 10 is a flow chart for explaining the operation of a measuring unit 24f of the image measuring section shown in FIG. 3.

FIG. 10 is a flow chart illustrating the operation of the measuring unit 24f. Referring to FIG. 10, in the measuring unit 24e, the test image data is inputted from the producing section 22 at a step SF1. The test image data is subjected to a density conversion process at a step SF2. In the density conversion process, the brightness of each pixel of the test image data is inverted, so that wire cords 211 of a breaker ply 210 are displayed as black lines. At a step SF3, an averaging process is executed to the brightness inverted image data. These processes are the same as the steps SC1 to SC3 in FIG. 7. Next, at a step SF4, the averaged image data is converted into a binary data. At a step SF5, a correcting process is executed to the binary image data. In the correcting process, the white stripe zone is set around each of the remained image lines for the wire cords 211a of the breaker ply 210a. That is, the image lines are changed to the white pixels. This process is the same as in the step SE6. AS a result, if the breaker plies 210 are correctly arranged, the screen will be white. In this manner, at a step SF6, whether an alien substance is introduced in the breaker ply or between breaker plies is determined based on whether the number of black pixels is more than a reference data as an allowance data which is read out from the storage unit 14. At a step SF7, the determining result is outputted to the CPU 26.

Figure 11:
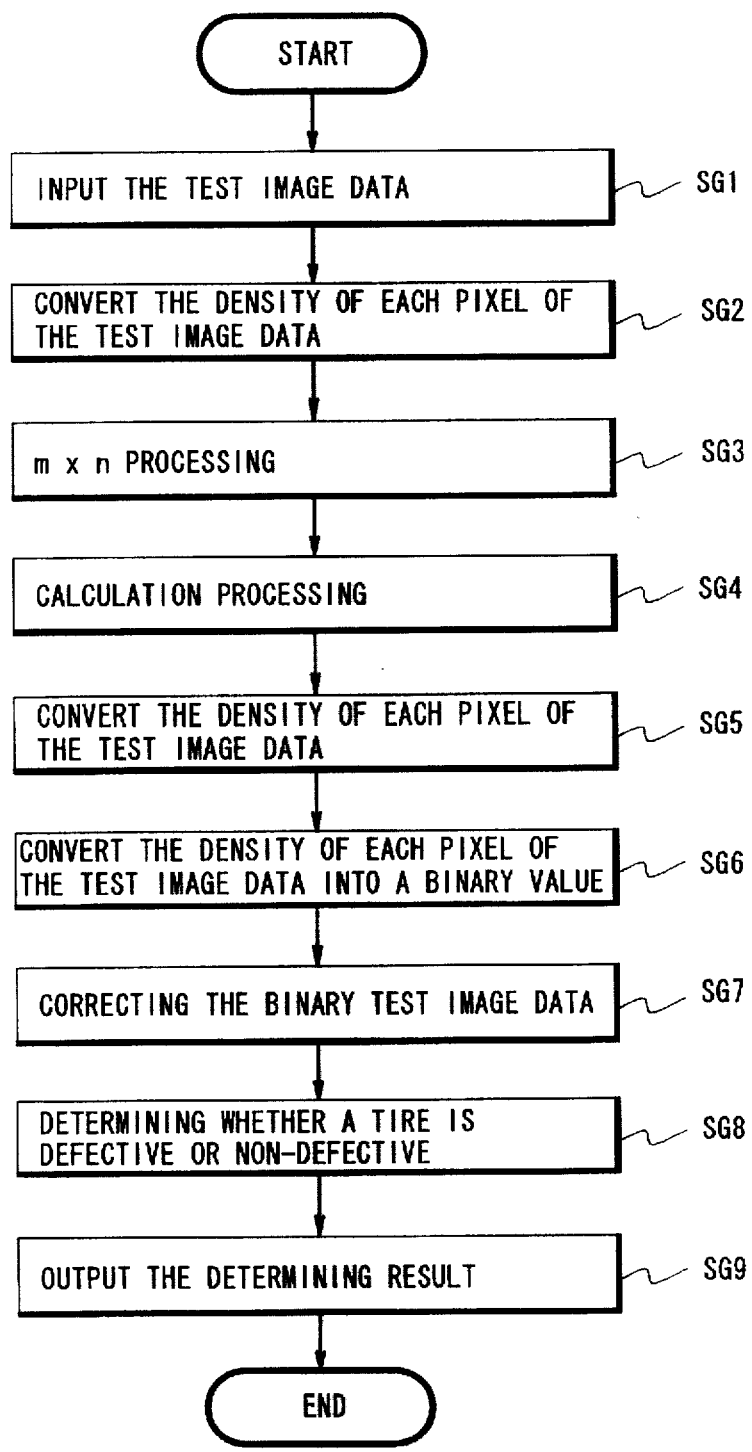
FIG. 11 is a flow chart for explaining the operation of a measuring unit 24g of the image measuring section shown in FIG. 3.

FIG. 11 is a flow chart illustrating the operation of the measuring unit 24g. Referring to FIG. 11, in the measuring unit 24g, the test image data is inputted from the producing section 22 at a step SG1. The test image data is subjected to a density conversion process at a step SG2. In the density conversion process, the brightness of each pixel of the test image data is converted with 1:1, so that the image lines of the wire cords are white lines. At a step SG3, an (m×n) process is executed. The image lines of the wire cords 211b of the breaker ply 211b are deleted through the (m×n) process. As a result, the image data for the breaker ply 210a can be extracted. After the (m×n) process, at a step SG4, the (m×n) processed image data is subtracted from the density converted image data obtained in the step SG2. The subtracted image data is again subjected to a density conversion process at a step SG5. In the density conversion process, the brightness of each pixel of the test image data is inverted, so that wire cords 211 of a breaker ply 210 are displayed as black lines. At a step SG6, the inverted image data is converted into a binary image data using a threshold value. Next, at a step SG7, a correcting process is executed to the binary image data as in the step SE6 of FIG. 9. In this manner, at a step SG8, whether the wire cords or rubber sections overlap is determined based on whether the number of black pixels is more than a reference data as an allowance data which is read out from the storage unit 14. At a step SG9, the determining result is outputted to the CPU 26.

Figure 12:
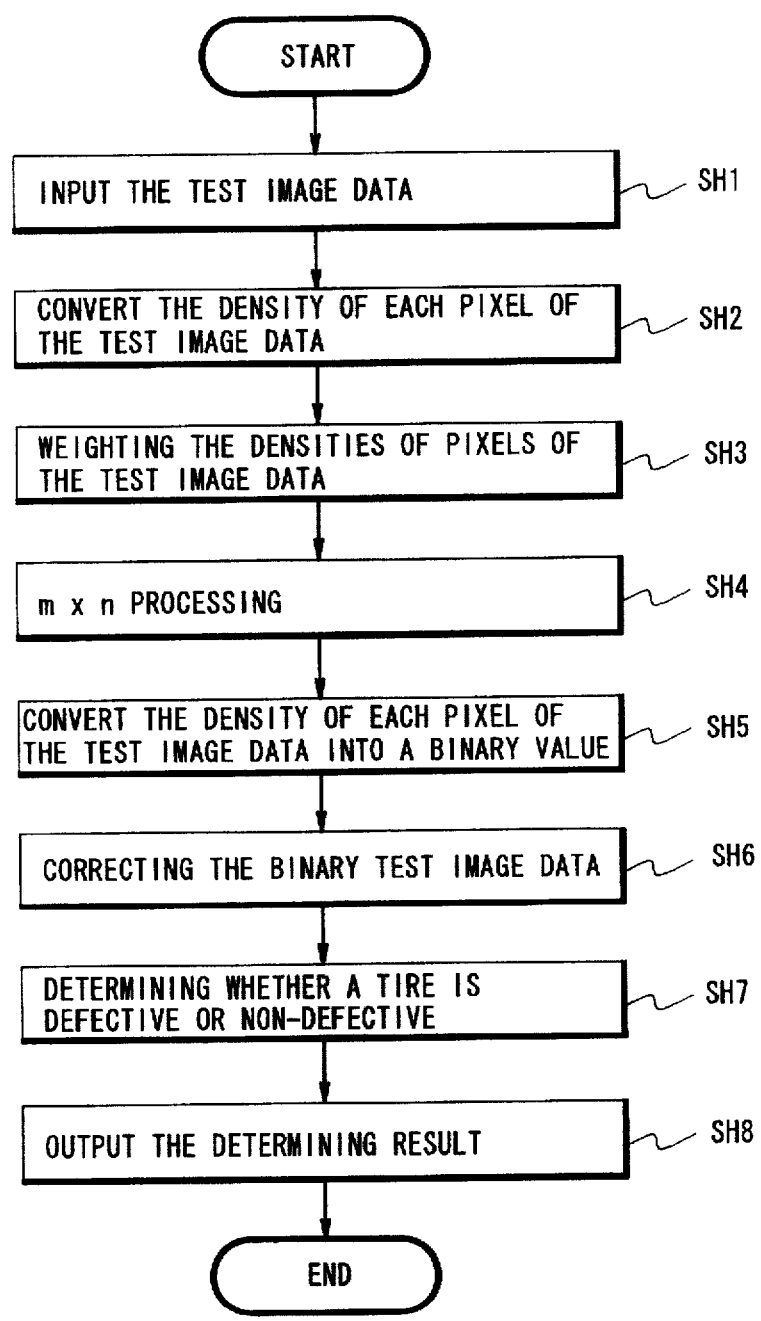
FIG. 12 is a flow chart for explaining the operation of a measuring unit 24h of the image measuring section shown in FIG. 3.

FIG. 12 is a flow chart illustrating the operation of the measuring unit 24h. Referring to FIG. 12, in the measuring unit 24h, the test image data is inputted from the producing section 22 at a step SH1. The test image data is subjected to density conversion process at a step SH2. In the density conversion process, the brightness of each pixel of the test image data is converted with 1:1, so that wire cords 211 of a breaker ply 210 are displayed as white lines. At this time, the abrupt change of density is checked. If there is the abrupt change of density, it means that two breaker plies overlap. At a step SH3, an averaging process is executed to the converted image data. These processes are the same as the steps SB1 to SB3 in FIG. 6. Next, at a step SH4, an (m×n) process is executed. In the (m×n) process, the densities of pixels in a region of (m×n) pixels are multiplied by predetermined coefficients, so that the image data is differentiated. As a result, the image data for one of the two breaker plies 210 can be extracted. After the (m×n) process, at a step SH5, the differentiated image data is converted into a binary image data using a threshold value. Next, at a step SH6, a correcting process is executed to the binary image data. These processes are the same as in the steps SA4 and SA5. In this manner, at a step SH7, whether one of two breaker plies 210 displaces from the other or whether the wire cords are displaced in the breaker ply in place is determined based on whether the number of black pixels is more than a reference data as an allowance data which is read out from the storage unit 14. At a step SH8, the determining result is outputted to the CPU 26.

In the above-mentioned measuring processes, a density of pixels for the carcass ply is different from that of pixels for the wire cords of the breaker ply 210a and the density of pixels for the wire cords of the breaker ply 210a is different from that of pixels for the wire cord of the breaker ply 211b, because the breaker ply 211b is attached on the breaker ply 210a. Therefore, the density conversion process is necessitated. Also, image lines for one of the breaker plies 210 is deleted through the differential process, or (m×n) process. In the correcting process, the image lines for the wire cords may be converted into white image lines or black image lines with a predetermined width. Thus, the defectiveness can be detected from the remaining pixels. Further, the calculation between the image data may be performed as in FIG. 11.

As described above, the measuring units 24a to 24h handle the test image data independently and output the determining results to the CPU 26. The CPU finally determines whether the tire is defective or non-defective, from these determining results from the measuring units 24a to 24h and outputs the final determining result to the display unit 10 and printer 16. The image data in each of the measuring units during the processing is stored in the memory 28 via the CPU 26. At the same time, the image data is displayed on the monitor 20 by switching the switch 18 in response to an input from the keyboard 12. By inputting a command from the keyboard 12 to the CPU 26, the image data can be printed by the printer 16, if necessary.

According to the present invention, in testing the arrangement of breaker plies and wire cords, the steps of a person in charge of test can be saved very much and the test precision can be increased.

In the embodiment, the image signal is directly supplied from the detector 8 to the circuit section 2. However, the image signal picked up by the detector is once stored in a video tape recorder and then the image data may be supplied from the video tape recorder.

As described above, according to the tire testing apparatus according to the present invention, a test image data having the contrast increased and a noise component removed can be obtained through pre-processing in the producing section 22. Further, through the density conversion process and filtering process, the contrast of the image data is further increased and the noise component is further removed. The filtered image data is converted into a binary image data and a data obtained from the binary image data is compared with the reference data to determine whether the internal structure of the tire is defective or non-defective. Therefore, high precision testing result can be obtained compared to the observation by eyes. At the same time, the testing processes can be automatically executed.

The measuring units 24a to 24h test different test items, respectively. That is, the measuring unit 24a determines whether linearity of the edge portion of a breaker ply 210 is distorted as shown in FIG. 22. The measuring unit 24b determines whether a wire cord 211 protrudes from the vertical edge portion of the breaker ply 210 as shown in FIG. 24. The measuring unit 24b determines whether a wire cord 211 protrudes from the vertical edge of the breaker ply 210 as shown in FIG. 24. The measuring unit 24c determines whether an excess space is present in a connection portion between two breaker plies 210 with the same orientation of wire cords 211 as shown in FIG. 19. The measuring unit 24d determines whether an overlapping portion is present in the connection portion between the two breaker plies 210 with the same orientation of wire cords 211 as shown in FIG. 18. The measuring unit 24e determines whether a wire cord 211 is broken at the edge portion of the breaker ply 210, whether the wire cords 211 are untied at the edge portion of the breaker ply, and whether two breaker plies are arranged inversely to each other in a lateral direction, as shown in FIGS. 21, 23, and 17. The measuring unit 24f determines whether an alien substance is introduced in a breaker ply 210 or between breaker plies 210 as shown in FIG. 26. The measuring unit 24g determines whether wire cords 211 or rubber sections overlap in a breaker ply 210, i.e., whether the breaker ply is defective or non-defective, as shown in FIG. 25. The measuring unit 24h determines whether a breaker ply 210 partially displaces in a lateral direction or two breaker plies displace, as shown in FIG. 20 and whether the breaker plies 210 overlap each other at one edge portion, as shown in FIG. 16. In this manner, the measuring units are operable independently and test the different test items, respectively. Therefore, the test time can be shortened.

What is claimed is:

1. A tire testing apparatus, for testing a tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, said apparatus comprising:

driving means for loading and holding a tire to a testing position in response to a test command, for intermittently rotating said tire at the test position in response to a rotate command such that a stationary test image can be generated, and for unloading said tire to a first position in response to a first unload command;

emitting means for emitting electromagnetic wave having a wavelength equal to or shorter than X-ray;

detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for outputting the test command to said driving means, for determining whether all the test portions of said tire are tested, when said tire is determined to be non-defective at said one test portion, for outputting the rotate command to said driving means for a next test portion if all the test portions of said tire are not yet tested, and for outputting the first unload command to said driving means if all the test portions are tested.

2. A tire testing apparatus according to claim 1, wherein said control means outputs a second unload command to said driving means when said tire is determined to be defective at the one test portion, and said driving means unloads said tire at a second position in response to the second unload command.

3. A tire testing apparatus according to claim 1, wherein said measuring means includes a plurality of measuring units for respectively measuring said tire on a plurality of test items, and said plurality of measuring units are operable independently from each other.

4. A tire testing apparatus according to claim 1, wherein said at least one test item is at least one of: whether breaker plies are arranged to have a linearity at an edge section of the breaker ply, whether any of the wire cords of the breaker ply protrudes from the edge section of the breaker ply, whether a gap greater than a predetermined value is present between breaker plies having the same wire cords orientation, whether the breaker plies having the same wire cords orientation overlap at a connection section of them, whether any of wire cords is broken or untied in the edge section of the breaker ply, whether the breaker plies of the pair are arranged inversely with respect to left and right positions, whether an alien substance is introduced in the breaker ply or between the breaker plies of the pair, whether displacement of one breaker ply from another breaker ply is present, and whether the wire cords or rubber sections overlap in the breaker ply.

5. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for converting the test image data into a binary image data and for determining whether the edge portion of the breaker ply is distorted, based on a line set on the binary image data.

6. A method of testing a tire, comprising the steps of:

loading a tire to a test position, a tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other;

irradiating electromagnetic wave having a wavelength equal to or shorter than X-ray to transmit a tread surface of one of test portions of said tire loaded at the test position;

detecting said electromagnetic wave to produce a test image signal;

executing a processing of at least one test item on said pair of breaker plies to a test image data; and automatically determining whether said tire is defective or non-defective, from the processing result of the test image data;

wherein said step of executing a processing includes:

adding an image signal corresponding to the transmitted electromagnetic wave for a predetermined frames to average the added image signal to produce the test image data;

inverting and enhancing a density of each of pixels of the test image data; and converting the enhanced image data into a binary 10 data.

7. A method according to claim 6, further comprising the steps of:

determining whether all the test portions of said tire are tested, when said tire is determined to be nondefective at said one test portion;

issuing a rotate command if all the test portions of said tire are not yet tested;

rotating said tire as in a practical use for a next test portion in response to the rotate command;

issuing a first unload command if all the test portions are tested; and unloading said tire at a first position in response to the first unload command.

8. A method according to claim 6, wherein said step of executing a processing includes weighting the pixel density of each pixel of the test image data while shifting a region having a predetermined size before said conversion into the binary image data.

9. A method according to claim 6, wherein said step of executing a processing includes:

after said conversion into the binary image data, converting intermittent pixel strings into a thick continuous pixel string with no default pixels and thinning the thick continuous pixel string.

10. A method according to claim 6, wherein said step of executing a processing include:

before said conversion into the binary image data, subtracting a reference image data obtained from the test image data from the test image data.

11. A method according to claim 6, wherein said step of executing a processing includes:

weighting pixels densities such that the densities of pixels in a first predetermined direction are increased and the densities of pixels in a second predetermined direction are decreased.

12. A method according to claim 6, wherein said step of executing a processing includes:

inverting the density of line image corresponding to the wire cords.

13. A method according to claim 6, wherein said step of automatically determining includes automatically determining whether said tire is defective or non-defective, by determining a distance from a pixel on a line predetermined on the test image data to a pixel of the breaker ply image the closest to the line and having the same y-coordinate, over all the pixels on the line.

14. A method according to claim 6, wherein said step of automatically determining includes automatically determining whether said tire is defective or non-defective, by counting a number of pixels remained on the processed test image data.

15. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for converting the test image data into a binary image data and for determining whether the edge portion of the breaker ply is distorted in part, whether the two breaker plies are displaced and arranged, or whether the two breaker plies overlap, based on a line set on the binary image data and change of the densities.

16. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for deleting pixels corresponding to the wire cords and for determining whether the wire cords or rubber sections overlap, based on an image data having the remaining pixels.

17. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for generating a reference image data from the test image data, for subtracting the reference image data from the test image data, and for determining whether the breaker ply is defective or non-defective, based on the subtracted image data.

18. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for inverting densities of pixels corresponding to the wire cords and for determining whether the breaker with the same orientation of the wire cords plies overlap, based on an image data having the inverted densities.

19. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for inverting densities of pixels corresponding to the wire cords for every predetermined distance and for determining whether the breaker plies with the same orientation of the wire cords overlap or whether the breaker plies provided to separate from each other, based on an image data having the inverted densities.

20. An apparatus for testing an internal structure of a tire, said tire including at least a pair of breaker plies disposed between a carcass and a tread, each of the breaker plies including a plurality of wire cords provided with a substantially constant gap between the wire cords, and an orientation of each wire cords in one of the breaker plies being different from that of each wire cords in the other, comprising:

an output unit for outputting a test result;

emitting means for emitting electromagnetic wave having a wavelength equal to or shorter than X-ray; detecting means for detecting said electromagnetic wave having transmitted one of test portions of said tire which is loaded at the test position, and for outputting the detecting result as a test image signal;

measuring means for receiving the test image signal from said detecting means, for executing a processing of at least one test item on said pair of breaker plies to produce a test image data corresponding to the test image signal, and for determining whether said pair of breaker plies is defective or non-defective, based on the processing result and a reference data for said at least one test item; and control means for controlling said emitting means, said detecting means and said measuring means for testing all the test positions, and for outputting to said output unit a data indicating that said tire is non-defective when said tire is determined to be non-defective at all the test positions;

wherein said measuring means includes a measuring unit for deleting pixels corresponding to the wire cords and for determining whether an alien substance is introduced, based on an image data having the inverted densities.

* * * * *